(12) United States Patent
Porat

(10) Patent No.: US 10,925,614 B2
(45) Date of Patent: Feb. 23, 2021

(54) UMBILICAL CORD CLAMPING AND CUTTING DEVICE

(71) Applicant: Amir Porat, Savyon (IL)

(72) Inventor: Amir Porat, Savyon (IL)

(*) Notice: Subject to any disclaimer, the term of this patent is extended or adjusted under 35 U.S.C. 154(b) by 146 days.

(21) Appl. No.: 16/046,409

(22) Filed: Jul. 26, 2018

(65) Prior Publication Data
US 2020/0029971 A1    Jan. 30, 2020

(51) Int. Cl.
*A61B 17/122*    (2006.01)
*A61B 17/32*    (2006.01)
*A61B 17/00*    (2006.01)

(52) U.S. Cl.
CPC ............ *A61B 17/122* (2013.01); *A61B 17/32* (2013.01); *A61B 2017/00477* (2013.01); *A61B 2017/320052* (2013.01)

(58) Field of Classification Search
CPC ..... A61B 17/122; A61B 17/128; A61B 17/32; A61B 17/42; A61B 17/083; A61B 17/11; A61B 17/068; A61B 2017/00477; A61B 2017/1225; A61B 2017/320052
USPC .................... 24/543; 606/151, 157, 158, 120
See application file for complete search history.

(56) References Cited

U.S. PATENT DOCUMENTS

2016/0151068 A1*   6/2016   Jensen ................. A61B 17/122
                                                                                                             606/157

FOREIGN PATENT DOCUMENTS

CN              2650714 Y   *   10/2004  ........... A61B 17/122

* cited by examiner

*Primary Examiner* — Katherine M Shi
*Assistant Examiner* — Alyssa M Keane
(74) *Attorney, Agent, or Firm* — The IP Law Firm of Guy Levi, LLC

(57) ABSTRACT

The disclosure is directed to clamping and cutting device for flexible, wet tubes. Specifically, the disclosure is directed to devices, kits and methods for selectably clamping an umbilical cord and only then cutting the cord, without the necessity of defining a mother side and/or baby side.

10 Claims, 7 Drawing Sheets

UMBILICAL CORD CLAMPING AND CUTTING DEVICE

BACKGROUND

The disclosure generally relates to clamping and cutting device for flexible, wet tubes. Specifically, the disclosure relates to devices, kits and methods for selectably clamping an umbilical cord and only then cutting the cord, without the necessity of defining a mother side and/or baby side.

Clamping and cutting an umbilical cord, where the clamping of umbilical clamps occurs simultaneously while advancing the blade between the closing clamps despite the serrated clamp surface are known. Often the cord slips along the clamp creating circumstances where clamping is incomplete. Moreover, dedicating certain clamp to the mother and certain clamp to the baby, can create confusion and force the design to favor certain dexterity, either left or right handed.

These and other shortcomings of the current state of affairs are addressed by the following description, drawings and claims.

SUMMARY

Disclosed, in various embodiments, are devices, kits and methods for selectably clamping an umbilical cord followed by cutting of the cord.

In an embodiment, provided herein is a device for clamping and cutting an umbilical cord by selectively moving between a first open position, an intermediate position and a cutting position comprising: a first and a second identical clamps, each clamp comprising an upper leg and a lower leg hingedly coupled at a proximal end of the legs, being sized and configured to receive and clamp a portion of the umbilical cord transverse to the cord; a clamps' support having a distal end and a proximal end comprising a blade, the clamps' support sized and configured for supporting the clamps side by side with the blade between them and for guiding the clamps to advance the blade between the clamps to cut the umbilical cord; and an elongated bar, slidably coupled to the clamps' support, sized and configured for guiding the clamps in a sliding movement within the clamps' support to advance the cutting means between the clamps to cut the umbilical cord, wherein the clamps' support is configured for selectably clamping each of the pair of clamps onto the umbilical cord.

In another embodiment, provided herein is a kit comprising: a first and a second identical clamps, each clamp comprising an upper leg and a lower leg hingedly coupled at a proximal end of the legs, being sized and configured to receive and clamp a portion of the umbilical cord transverse to the cord; a clamps' support having a distal end and a proximal end comprising a blade, the clamps' support sized and configured for supporting the clamps side by side with the blade between them and for guiding the clamps to advance the blade between the clamps to cut the umbilical cord; and an elongated bar, slidably coupled to the clamps' support, sized and configured for guiding the clamps in a sliding movement within the clamps' support to advance the cutting means between the clamps to cut the umbilical cord, wherein the clamps' support, wherein the clamps' support is configured for selectably clamping each of the pair of clamps onto the umbilical cord, wherein the first and a second identical clamps, the clamps' support and the elongated bar are capable of being assembled to form a device for clamping and cutting an umbilical cord by selectively moving between a first open position, an intermediate position and a cutting position.

In yet another embodiment, provided herein is a method of clamping and cutting an umbilical cord, the method comprising providing a device for clamping and cutting an umbilical cord by selectively moving between a first open position, an intermediate position and a cutting position comprising: a first and a second identical clamps, each clamp comprising an upper leg and a lower leg hingedly coupled at a proximal end of the legs, being sized and configured to receive and clamp a portion of the umbilical cord transverse to the cord; a clamps' support having a distal end and a proximal end comprising a blade, the clamps' support sized and configured for supporting the clamps side by side with the blade between them and for guiding the clamps to advance the blade between the clamps to cut the umbilical cord; and an elongated bar, slidably coupled to the clamps' support, sized and configured for guiding the clamps in a sliding movement within the clamps' support to advance the cutting means between the clamps to cut the umbilical cord, wherein the clamps' support is configured for selectably clamping each of the pair of clamps onto the umbilical cord; placing the umbilical cord between the first and second clamps upper and lower legs; using the clamps support, clamping the clamps over the umbilical cord; using the elongated bar, slidably advancing the clamps against the blade thus cutting the cord; and removing the first and second clamps from the clamps' support.

These and other objectives and advantages of the present technology will become understood by the reader and it is intended that these objects and advantages are within the scope of the present invention. To the accomplishment of the above and related objects, this disclosure may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE FIGURES

For a better understanding of the assemblies, kits and methods for converting at least one of a functional or nonfunctional Presta-type valve to a Schrader-type valve member in the various embodiments thereof, reference is made to the accompanying drawings, in which like numerals designate corresponding elements or sections throughout and in which.

DESCRIPTION

Figure 1A:
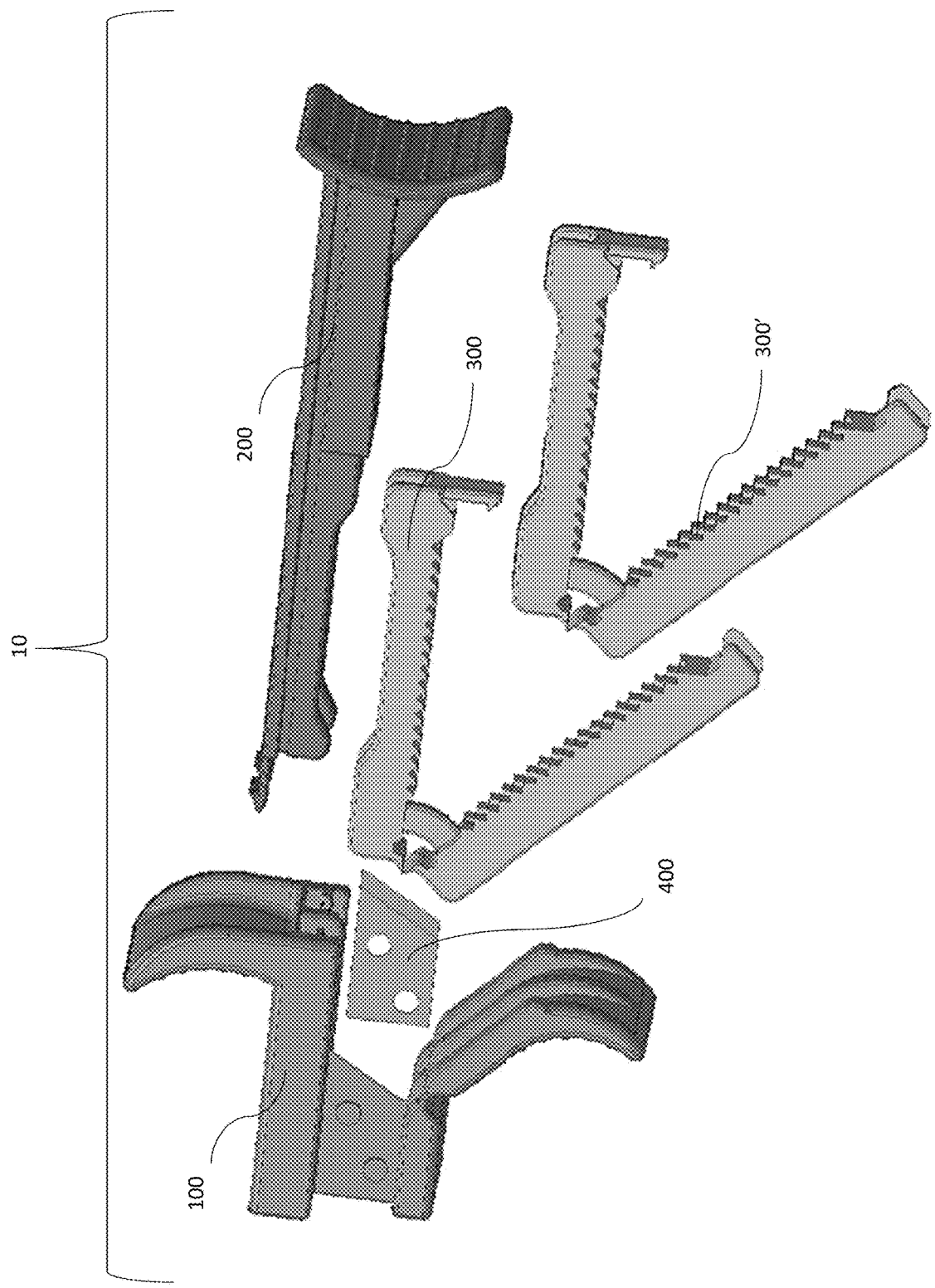
FIG. 1A is an exploded view of the device, with an isometric view of the assembled device illustrated in FIG. 1B.

Provided herein are embodiments of devices, kits and methods for clamping and cutting an umbilical cord by selectively moving between a first open position, an intermediate position and a cutting position using symmetrical clamps.

Accordingly and in an embodiment, provided herein is a a device for clamping and cutting an umbilical cord by selectively moving between a first open position, an intermediate position and a cutting position comprising: a first and a second identical clamps, each clamp comprising an upper leg and a lower leg hingedly coupled at a proximal end of the legs, being sized and configured to receive and clamp a portion of the umbilical cord transverse to the cord; a clamps' support having a distal end and a proximal end comprising a blade, the clamps' support sized and configured for supporting the clamps side by side with the blade between them and for guiding the clamps to advance the blade between the clamps to cut the umbilical cord; and an elongated bar, slidably coupled to the clamps' support, sized and configured for guiding the clamps in a sliding movement within the clamps' support to advance the cutting means between the clamps to cut the umbilical cord, wherein the clamps' support is configured for selectably clamping each of the pair of clamps onto the umbilical cord.

The clamps' support comprises: an apically curved wing extending apically from an upper surface; a first basally open channel defined between a first side wall, the upper surface and a central wall sized and configured to slidably accommodate a portion of the first clamp's upper leg, the first basally open channel having a first shelf partially extending centrally from the first side wall spanning the length of the first channel; a second basally open channel defined between a second side wall, the upper surface and a central wall sized and configured to slidably accommodate a portion of the second clamp's upper leg, the second basally open channel having a second shelf partially extending centrally from the second side wall spanning the length of the second channel; a lower surface disposed basal and perpendicular to the central wall, the lower surface having a third apically open channel defined between a third side wall, the lower surface and the central wall, sized and configured to slidably accommodate a first portion of the first clamp's lower leg, and a fourth apically open channel defined between a fourth side wall, the lower surface and the central wall, sized and configured to slidably accommodate a first portion of the second clamp's lower leg; a blade coupled to the central wall; and a basally curved wing hingedly coupled to the lower surface, the basally curved wing having an upper surface and a lower surface, the upper surface having a fifth apically open channel defined between a fifth side wall, the upper surface of the basally curved wing and a median sized and configured to slidably accommodate a second portion of the first clamp's lower leg, and a sixth apically open channel defined between a sixth side wall, the upper surface of the basally curved wing and a median sized and configured to slidably accommodate a second portion of the second clamp's lower leg, wherein the basally curved wing is configured, when rotated to selectable cause the lower leg of each of the first and second clamp to be engaged by the upper leg of each of the first and second clamps.

In an embodiment, the term "slidably coupled" is used in its broadest sense to refer to elements which are coupled in a way that permits one element to slide or translate with respect to another element. Furthermore, "Hingedly coupled" indicates that the orientation of one component relative to the other can be varied. This may be because of a connecting region which permits bending, or because of a form of mechanical connection that permits relative movement, for example a pivot or a hinge pin. There may be an intermediate portion which is hinged at respective spaced locations to the first and second portions, allowing a greater degree of hinging in one or more directions. A hinging device may be lockable. Hinged portions may be separable. Thus, the invention envisages a modular system, in which a user may choose from a range of first portions and a range of second portions which can be connected together hingably.

The terms "engage", "engaged" and various forms thereof, when used with reference to the various components disclosed as engaging or engaged, refer to the application of any forces that tend to hold the engaged components together against inadvertent or undesired separating forces (e.g., such as may be introduced during compression of the clamps onto the umbilical cord). It is to be understood, however, that engagement does not in all cases require an interlocking connection that is maintained against every conceivable type or magnitude of separating force.

A more complete understanding of the components, methods, and devices disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof, their relative size relationship and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure.

In the drawings and the following description below, it is to be understood that like numeric designations refer to components of like function. Likewise, cross sections are referred to on normal orthogonal coordinate apparatus having XYZ axis, such that Y axis refers to front-to-back, X axis refers to side-to-side, and Z axis refers to up-and-down.

Turning now to FIGS. 1A-4B, illustrating in FIG. 1A, an exploded view of device 10 for clamping and cutting an umbilical cord by selectively moving between a first open position, an intermediate position and a cutting position comprising: first and a second identical clamps 300, 300', each clamp comprising upper leg 301 and lower leg 302 hingedly coupled 305 at proximal ends 304, 314 of the upper leg and lower leg respectively, being sized and configured to receive and clamp a portion of umbilical cord 700 (not shown) transverse to cord 700. Also illustrated in FIGS. 1A, 1B, 2A, and 2B is clamps' support 100 having distal end 101 and proximal end 102 comprising blade 400. Clamps' support 100 can be sized and configured for supporting first and second clamps 300, 300' (see e.g., FIG. 1B) side by side with blade 400 between them and clamps' support 100 also can be configured for guiding first and second clamps 300, 300' to advance blade 400 distally between first and second clamps 300, 300', to cut umbilical cord 700. FIGS. 1A, 1B, 3A, and 3B further illustrate elongated bar 200, slidably coupled to clamps' support 100, sized and configured for guiding first and second clamps 300, 300' in a sliding movement within clamps' support 100 to advance blade 400 between first and second clamps 300, 300' to cut umbilical cord 700, wherein clamps' support 100 can be configured for selectably clamping each of first and second clamps 300, 300' onto umbilical cord 700.

Figure 2A:
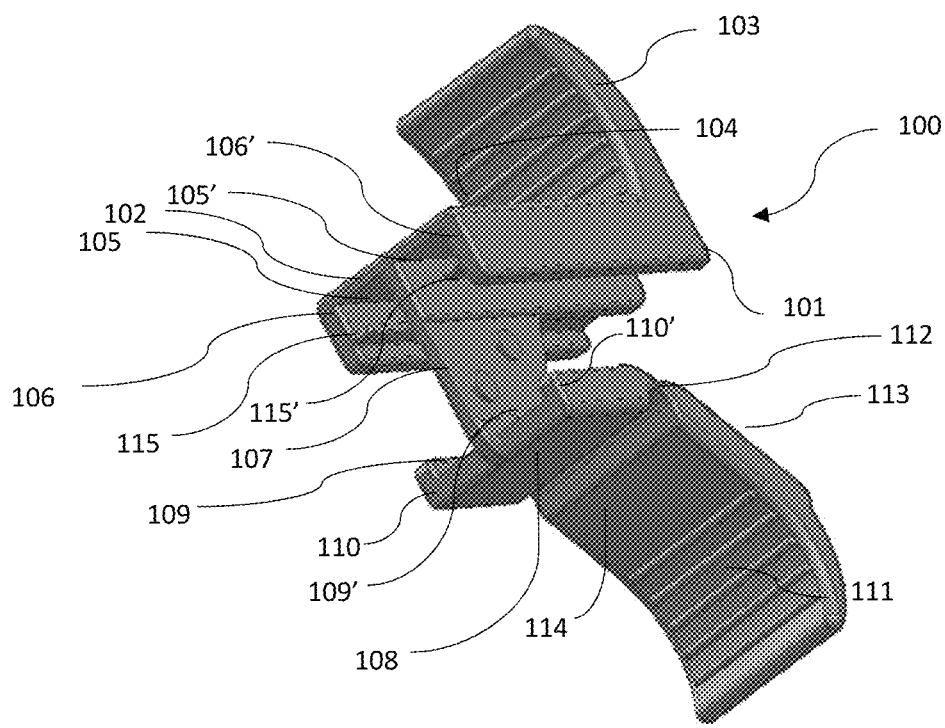
FIG. 2A is a proximal bottom isometric view of the clamps' support member, with a top distal isometric view shown in FIG. 2B.
Figure 2B:
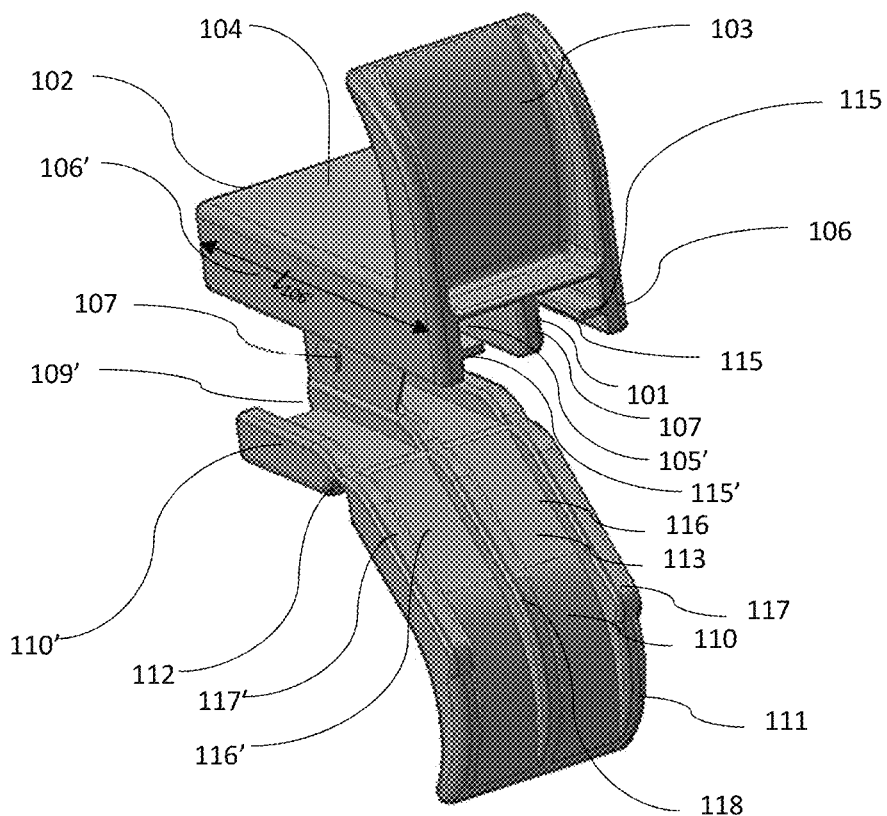
Figure 5:
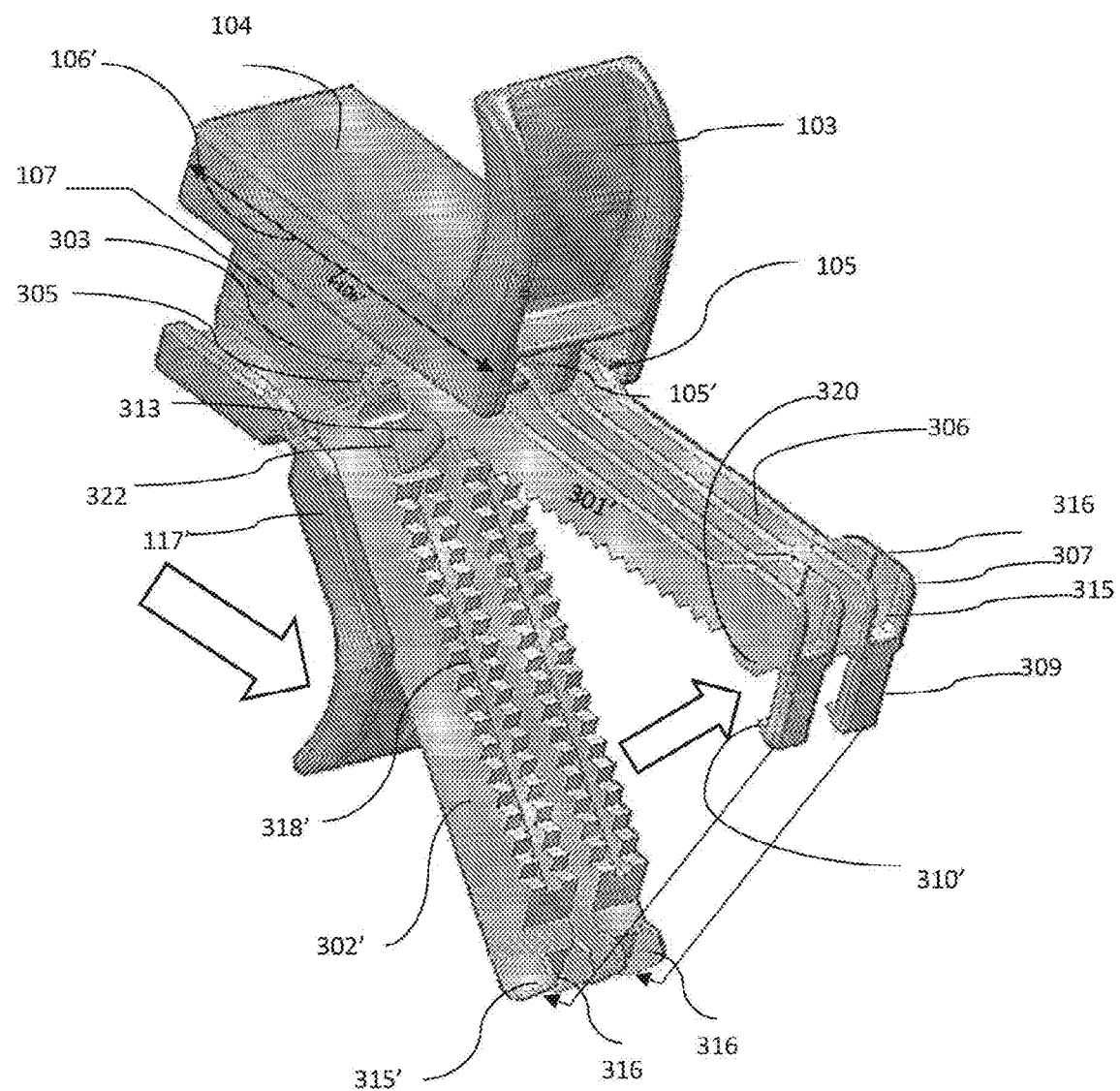
FIG. 5 is an illustration of the clamps in the clamps' support.

Turning now to FIGS. 2A, 2B and 5, illustrating clamps' support 100 member and showing clamps' support 100 member as further comprising apically curved wing 103 extending apically from upper surface 104 (see e.g., FIG. 2B), with first basally open channel 105 defined between first side wall 106, upper surface 104 and central wall 107, first channel 105 sized and configured to slidably accommodate a portion of first clamp's 300 upper leg 301. First basally open channel 105, further having first shelf 115 partially extending centrally from first side wall 106 spanning the length of first channel 105. Also shown is second basally open channel 105' defined between second side wall 106', upper surface 104 and central wall 107, second basally open channel 105' also sized and configured to slidably accommodate a portion of second clamp's 300' upper leg 301', second basally open channel 105' having second shelf 115' partially extending centrally from second side wall 106' likewise spanning the length of second basally open channel 105'. Clamps' support 100 further comprises lower surface 108 disposed basal and perpendicular to central wall 107 (onto which, blade 400 extending distally is coupled), lower surface 108 having third apically open channel 109 defined between third side wall 110, lower surface 108 and central wall 107, apically open channel 109 sized and configured to slidably accommodate a first portion of first clamp's 300 lower leg 302, and fourth apically open channel 109' defined between fourth side wall 110', lower surface 108 and central wall 107, sized and configured to slidably accommodate a first portion of second clamp's 300' lower leg 302'. Blade 400, can be coupled to central wall 107, be beveled and extend distally. In addition, basally curved wing 111 hingedly coupled 112 to lower surface 108. Basally curved wing 111 having upper surface 113 and lower surface 114, with upper surface 113 having fifth apically open channel 116 defined between fifth side wall 117, upper surface 113 of basally curved wing 111 and median 118 sized and configured to slidably accommodate a second portion of first clamp's 300 lower leg 302. Upper surface further comprises sixth apically open channel 116' defined between sixth side wall 117, upper surface 113 of basally curved wing 111 and median 118, sized and configured to slidably accommodate a second portion of second clamp's 300' lower leg 302'. Basally curved wing is configured, when rotated (see e.g., FIG. 5) about hinge 112, which in an embodiment, is a live hinge, to selectably (in other words, without affecting the operation of other components) to cause lower leg 302, 302' of each of first and second clamps 300, 300' to be engaged by upper leg 301, 301' of first and second clamps 300, 300'.

Figure 1B:
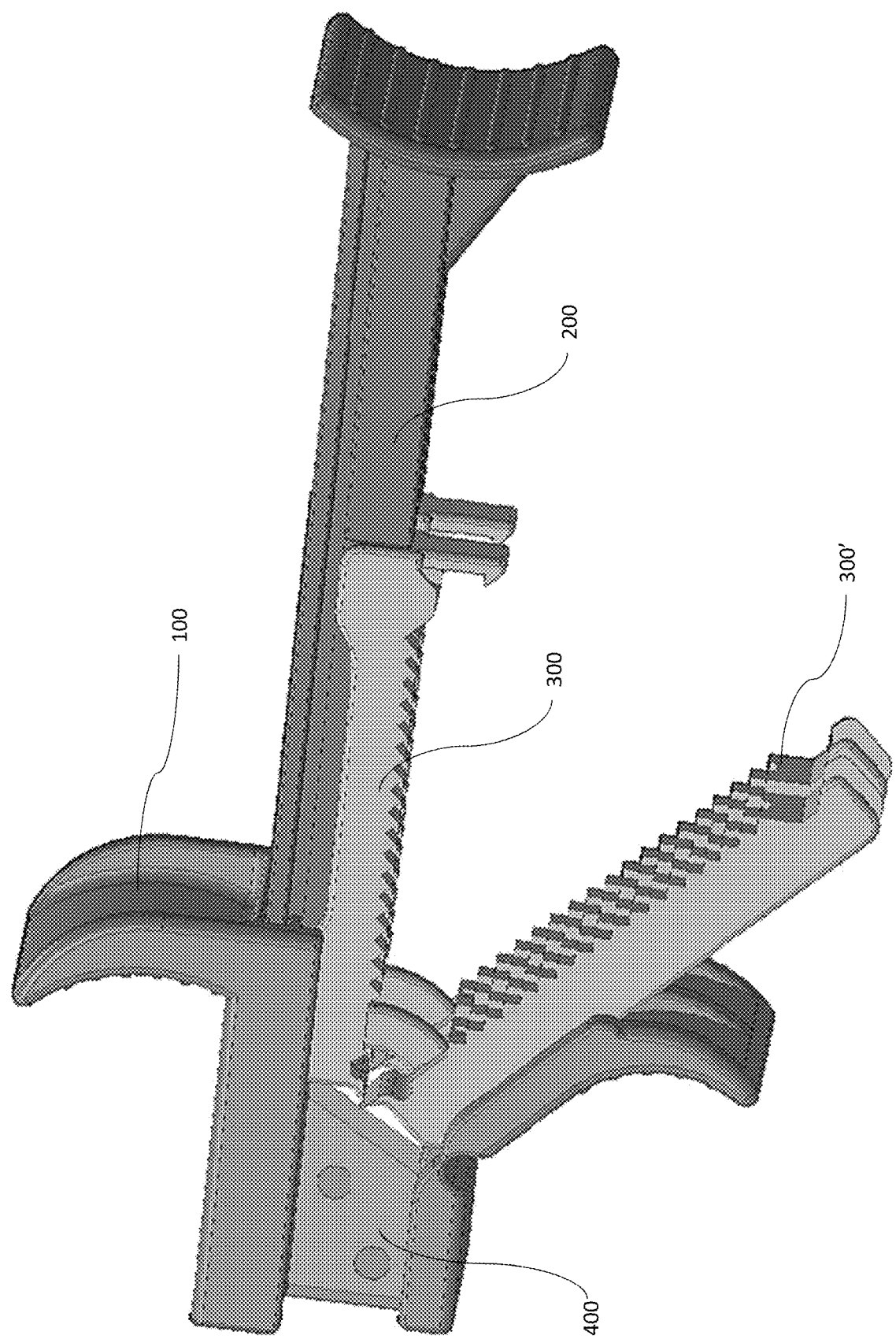

Turning now to FIGS. 1A, 1B, 4A, 4B and 5, wherein upper leg 301, 301 of each of clamps 300, 300' having distal end 303 (with corresponding numbering on second clamp 300', e.g., 303') and proximal end 304 and further comprising: apically open channel 306 having open distal 307 end and closed proximal end 308 configured to accommodate a portion of elongated bar 200 (see e.g., FIG. 1B). Upper leg 301 having basally extending tab 309 disposed at distal end 303 of upper leg 301. Tab 309 having hooked end 310 configured to engage abutment 315 (see e.g., FIG. 4A) disposed at distal end 330 of lower leg 302. Upper leg 301 of first 300 (and second 300') clamp, further having first 311 and second 331 basally extending serrated surface to assist with engaging umbilical cord 700 (not shown) whereby first 311 and second 331 basally extending serrated surface are separated by slot 312. As shown and in an embodiment, first 311 and second 331 basally extending serrated surface(s) are sized to span a substantial (e.g., more than 60%) portion of upper leg 301. Upper leg also has basally extending arcuate guide rail 313, disposed proximal to first 311 and second 331 basally extending serrated surface(s).

In addition, lower leg 302 of first and second clamps 300, 300' having a distal end 330 and a proximal end 314 further comprise abutment 315 disposed at distal end 330 of lower leg 302, sized and configured to engage hooked end 310 of tab 309, with distally extending walls 316, 336 disposed at distal end 330 of lower leg 302, defining passage 324 configured to accommodate a portion of tab 309. Lower leg 302 of first and second clamps 300, 300' further comprises first 318 and second 338 apically extending serrated surface(s) separated by slot 319, first 318 and second 338 apically extending serrated surface(s) of lower leg 302 sized to span a substantial portion (e.g., more than 60%) of lower leg 302, wherein lower leg further defines arcuate well 322, disposed proximal to first 318 and second 338 apically extending serrated surface(s) of lower leg 302 of first and second clamps 300, 300', where arcuate well 322 sized and configured to accommodate basally extending arcuate guide rail 313. Guide rail 313 configured to provide an axis for the partial rotation motion (see e.g., FIG. 5) when clamping first and second clamps 300, 300' onto umbilical cord, to ensure first 311 and second 331 basally extending serrated surface(s) are aligned with first 318 and second 338 apically extending serrated surface(s), thus creating a better seal of umbilical cord 700, or any other flexible tube or body lumen (e.g., small intestine, blood vessel). Guide rail 313 can also serve as a stop for umbilical cord 700.

Figure 3A:
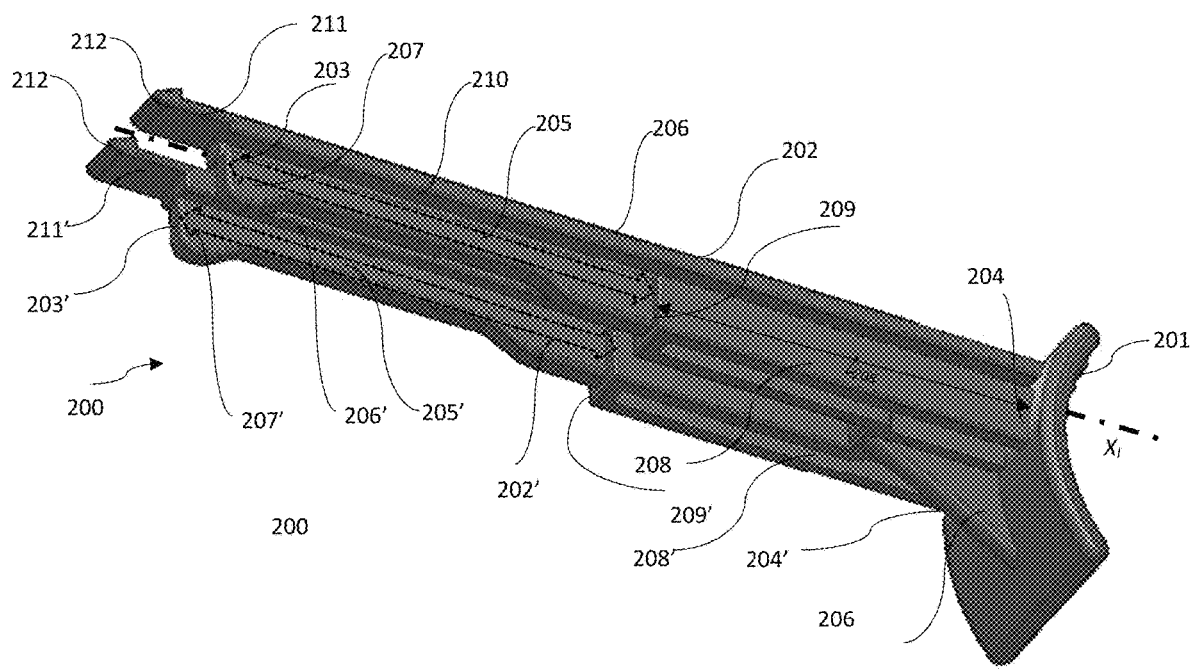
FIG. 3A is an isometric view of the elongated bar along the longitudinal axis with a proximal isometric view illustrated in FIG. 3B.
Figure 3B:
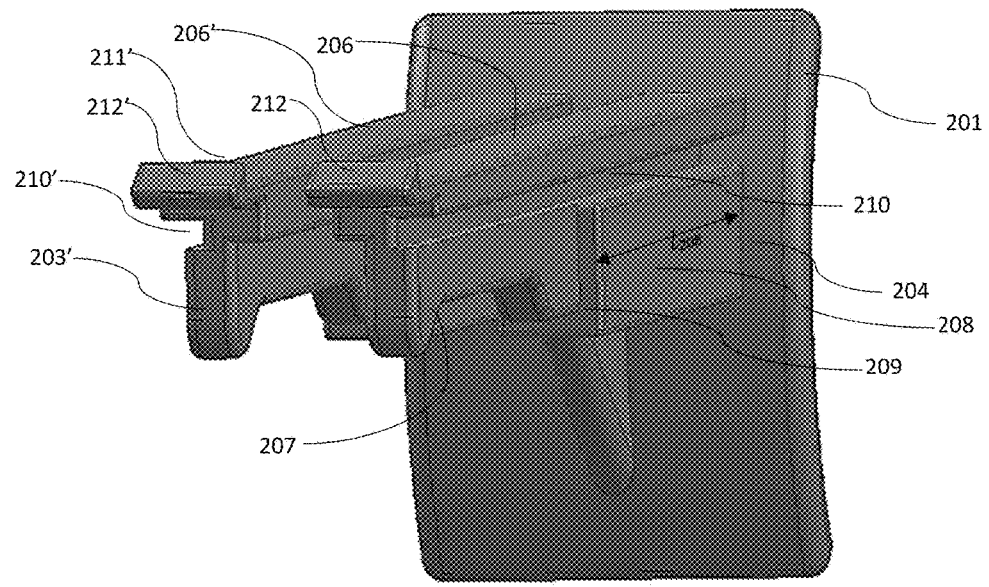
Figure 4A:
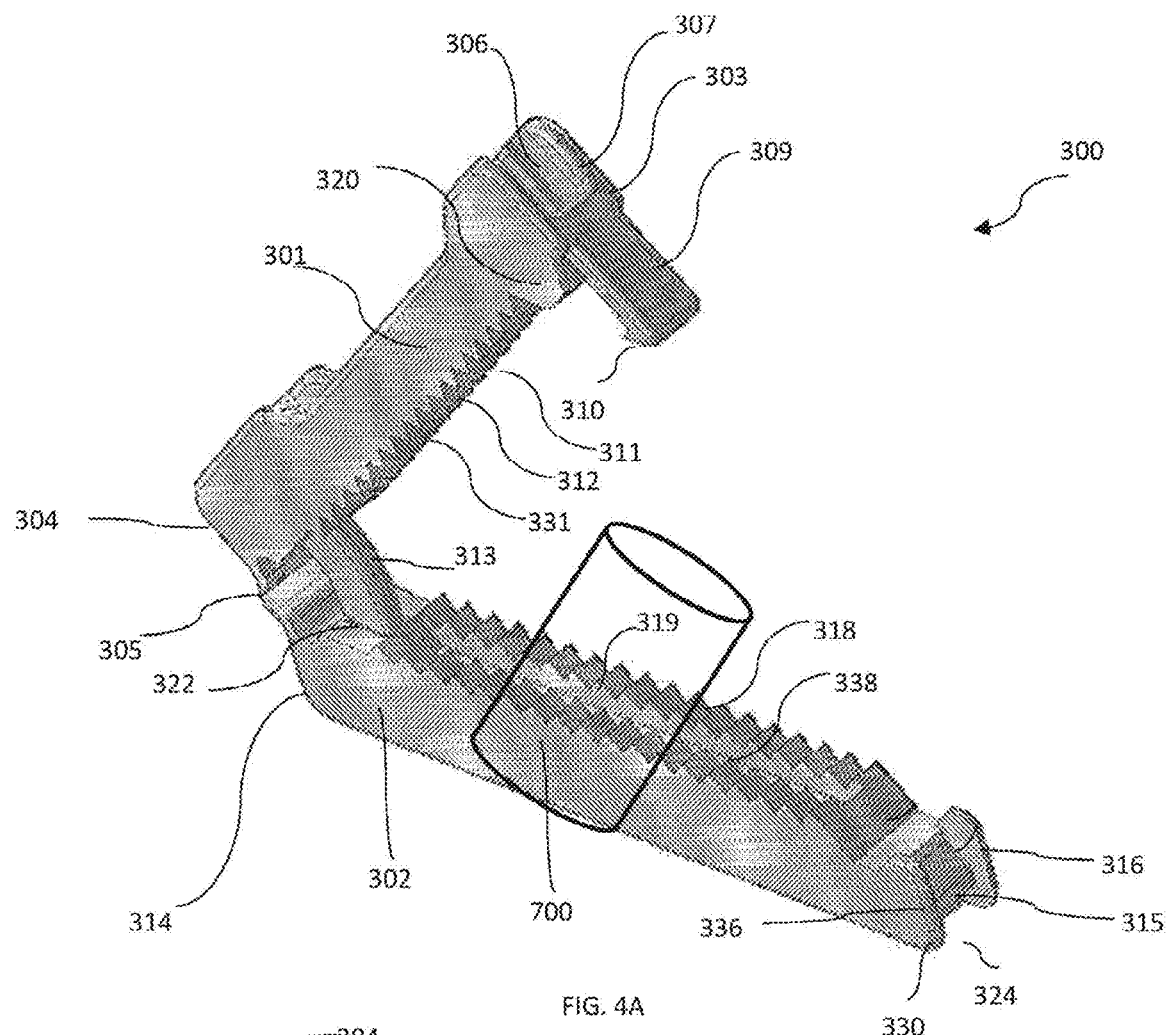
FIG. 4A illustrates a top isometric view of the first and second clamps with another top isometric view illustrated in FIG. 4B.
Figure 4B:
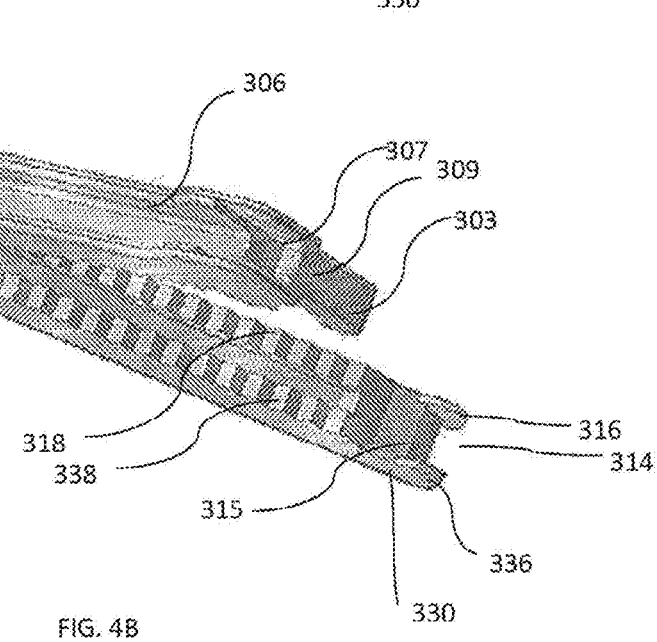

Elongated bar 200 of device 10 and kit capable of being assembled to form device 10 with or without first and second clamps 300, 300', is illustrated in FIGS. 1A, 1B, 3A, and 3B and as illustrated in an embodiment, comprises: first 202 and second 202' beams extending proximally from distally curved panel 201 along longitudinal axis $X_1$, each of first 202 and second 202' beams having: distal end 204, 204' and proximal end 203, 203' defining a T-shaped cross section. Each of first 202 and second 202' beam(s) further comprises proximal portion 205, 205' extending basally from cross bar 206 of T-shaped cross section, forming proximal rail having a protrusion 207, 207' at proximal rails proximal end 203, 203' that is configured to enter and abut closed proximal end 308, 308' of apically open channel 306, 306' of upper leg 301, 301' of each of first 300 and second 300' clamps. As illustrated in FIGS. 3A, 3B distal portion 208, 208' that is wider than proximal rail 205, 205', defining ledge 209, 209' configured and sized to abut distal end 303, 303' of upper leg 301, 301' of each of first 300 and second 300' clamps. As shown in FIG. 3B, slot 210, 210' spans the length of both proximal rail 205, 205' and distal portion 208, 208' configured to slidably couple to each of first 315 and second 315' shelf centrally extending from first 106 and second 106' side walls of clamps' support 100. Elongated bar 200 further comprises resilient flat extension 211, 211' having an apically protruding lip 212, 212' extending from proximal end 203, 203' of beam's cross bar 206, 206'. Cross bar(s) 206, 206' being sized and configured to be accommodated in first 105, and second 105' basally open channels of first and second clamps 300, 300' of clamps' support 100. Distal portion 208, 208' of elongated bar 200 is sized to have length $l_{208}$ ($l_{208'}$), that is longer than the length of first and second side walls $l_{106}$, $l_{106'}$.

Initially, when clamping umbilical cord 700, by compressing basally curved wing 111 hingedly coupled 112 to lower surface 108 about hinge 112, will cause tabs 309, 309' to engage abutments 315, 315' to clamp umbilical cord 700

(see e.g., FIG. 4A, 6A-6C). The clamping can be done separate and distinct from advancing first and second clamps 300, 300' with clamps' support 100, by pulling apically curved wing 103 and basally curved wing 111 distally against distally curved panel 201 of elongated bar 200, with proximal rail portions 205, 205' having a protrusion 207, 207' abutting closed proximal end 308, 308' of apically open channel 306, 306' of upper leg 301, 301' of each of first 300 and second 300' clamps thus advancing first and second clamps 300, 300' against blade 400 and cutting cord 700 (see e.g., FIG. 6A).

Figure 6A:
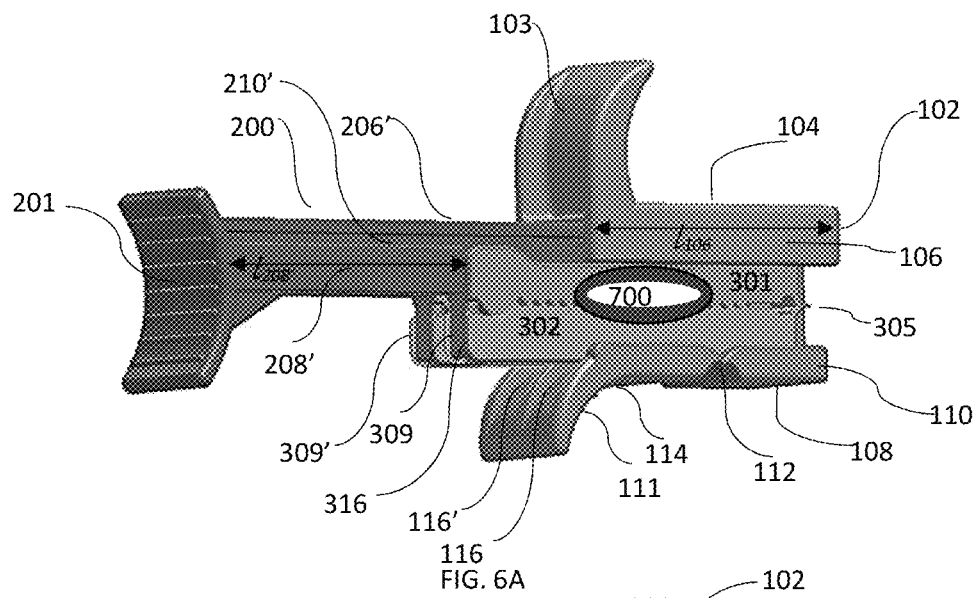
FIG. 6A illustrates the initial clamping of the clamps, the sliding of the clamps in FIG. 6B and the release of the clamps in FIG. 6C.
Figure 6B:
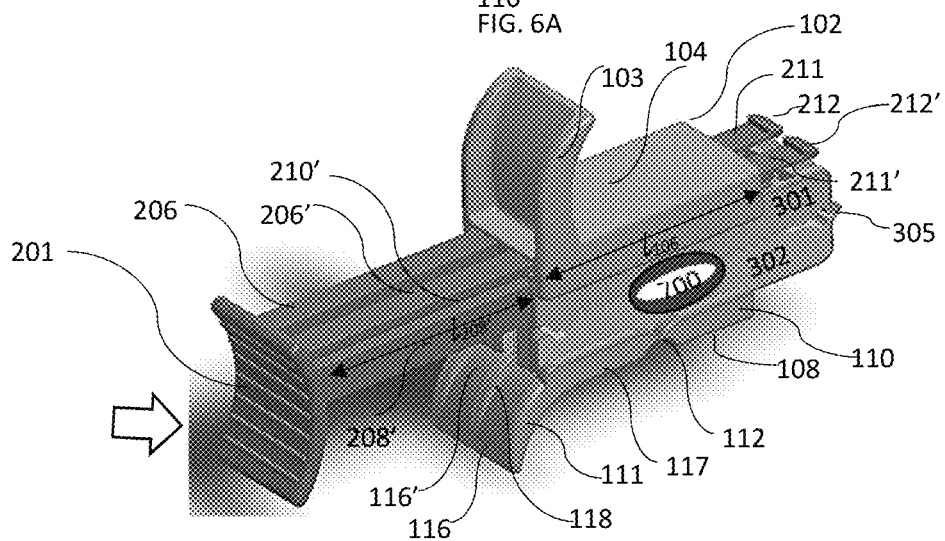
Figure 6C:
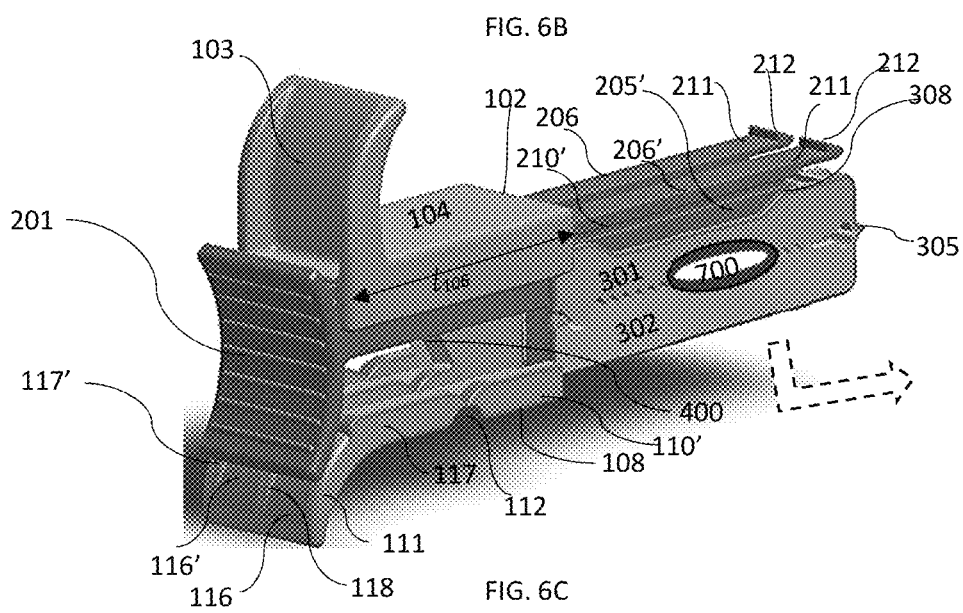

Turning now to FIGS. 6A-6C, illustrating the progress of the clamped umbilical cord 700 in device 10. As illustrated in FIG. 6A, clamping of first and second (identical) clamps 300, 300' is affected by simultaneously rotating basally curved wing 111 on hinge 112 against first and second lower leg 302, 302' disposed in fifth and sixth apically open channels 116, 116', clamping umbilical cord therebetween by engaging tabs 309, 309' with hooked ends 310, 310' on abutments 315, 315'. Moving on to FIG. 6B, pulling on apically curved wing 103 simultaneously with basally curved wing 111, against distally curved panel 201, will cause elongated bar 200 to slidably translate forward, causing first and second clamps 300, 300' to slide proximally by having proximal portion 205, 205' extending basally from cross bar 206, 206' of T-shaped cross section, with proximal rail protrusion 207, 207' abut closed proximal end 308, 308' of apically open channel 306, 306' of upper leg 301, 301' of each of first 300 and second 300' clamps, thus moving the now clamped umbilical cord 700 against the static blade 400 (See e.g., FIG. 6C). As illustrated in FIG. 6C, the length of distal portion 208, 208' marked as $l_{208'}$, is longer than the length of first and second walls 106, 106', marked as $l_{106}$, ($l_{208'}>l_{106}$) such that at the end of the cutting, when apically curved wing 103 simultaneously with basally curved wing 111 abut the proximal surface of distally curved panel 201, third, fourth, fifth and sixth apically open channels 109, 109', 116, 116' no longer support lower legs 302, 302' of first and second clamps 300' 300' allowing rails of proximal portion 205, 205' to be removed from apically open channel 306, 306' of upper leg 301, 301' of each of first 300 and second 300' clamps, thus releasing device 10.

In an embodiment, the kits provided herein are capable of being assembled to form the device disclosed, either with, or without the clamps which can be obtained separately.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "member" or "element" when used in the singular refers to a single integrated part that moves as a unit and does not include a plurality of parts with independent and separate movement between. In other words, as used herein, the terms "member" or "element" can be made of several pieces to foam an integral unit, but does not include two or more parts with a first part that moves relative to a second part.

The terms "bottom", "below", "top" and "above" as used herein do not necessarily indicate that a "bottom" component is below a "top" component, or that a component that is "below" is indeed "below" another component or that a component that is "above" is indeed "above" another component. As such, directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

Likewise, directional terms "proximal", "distal", "longitudinal" "lateral", "apical", "axial", "radial" and "transverse" as well as any other similar directional terms are merely used for convenience in describing the various embodiments of the present invention. Finally, terms of degree such as "substantially", "about" and "approximately" as used herein mean a reasonable amount of deviation of the modified term such that the end result is not significantly changed.

While particular embodiments have been described, alternatives, modifications, variations, improvements, and substantial equivalents that are or may be presently unforeseen may arise to applicants or others skilled in the art. Accordingly, the appended claims as filed and as they may be amended, are intended to embrace all such alternatives, modifications variations, improvements, and substantial equivalents.

What is claimed:

1. A device for clamping and cutting an umbilical cord by selectively moving between a first open position, an intermediate position and a cutting position comprising:
   a. a first and a second identical clamps, each clamp comprising an upper leg and a lower leg hingedly coupled at a proximal end of the legs, being sized and configured to receive and clamp a portion of the umbilical cord transverse to the cord;
   b. a clamps' support having a distal end and a proximal end comprising a blade, the clamps' support sized and configured for supporting the clamps side by side with the blade between them and for guiding the clamps to advance the blade between the clamps to cut the umbilical cord, wherein the clamps' support comprises:
      a lower surface disposed basal and perpendicular to the central wall, and
      a basally curved wing hingedly coupled to the lower surface, wherein the basally curved wing is configured, when rotated to selectable cause the lower leg of each of the first and second clamps to be engaged by the upper leg of each of the first and second clamps; and
   c. an elongated bar, slidably coupled to the clamps' support, sized and configured for guiding the clamps in a sliding movement within the clamps' support to advance the blade between the clamps to cut the umbilical cord, wherein the clamps' support is configured for selectably clamping each of the pair of clamps onto the umbilical cord.

2. The device of claim 1, wherein the clamps' support further comprises:
   an apically curved wing extending apically from the upper surface;
   a first basally open channel defined between a first side wall, the upper surface and a central wall, sized and configured to slidably accommodate a portion of the first clamp's upper leg, the first basally open channel having a first shelf partially extending centrally from the first side wall spanning the length of the first basally open channel;
   a second basally open channel defined between a second side wall, the upper surface and the central wall, sized and configured to slidably accommodate a portion of the second clamp's upper leg, the second basally open channel having a second shelf partially extending centrally from the second side wall spanning the length of the second basally open channel;

wherein the lower surface has a third apically open channel defined between a third side wall, the lower surface and the central wall, sized and configured to slidably accommodate a first portion of the first clamp's lower leg, and a fourth apically open channel defined between a fourth side wall, the lower surface and the central wall, sized and configured to slidably accommodate a first portion of the second clamp's lower leg; and a blade coupled to the central wall;

wherein the basally curved wing has an upper surface and a lower surface, the upper surface having a fifth apically open channel defined between a fifth side wall, the upper surface of the basally curved wing and a median sized and configured to slidably accommodate a second portion of the first clamp's lower leg, and a sixth apically open channel defined between a sixth side wall, the upper surface of the basally curved wing and a median sized and configured to slidably accommodate a second portion of the second clamp's lower leg.

3. The device of claim 2, wherein the upper leg of each of the first and second clamps having a distal end and a proximal end, further comprising:
   a. an apically open channel having an open distal end and a closed proximal end configured to accommodate a portion of the elongated bar;
   b. a basally extending tab disposed at the distal end of the upper leg, the tab having a hooked end configured to engage an abutment disposed at a distal end of the lower leg;
   c. a first and a second basally extending serrated surface separated by a slot, the first and second serrated surface spanning a substantial portion of the upper leg; and
   d. a basally extending arcuate guide rail disposed proximal to the first and second serrated surfaces.

4. The device of claim 3, wherein the lower leg of each of the first and second clamps having a distal end and a proximal end further comprising:
   a. the abutment disposed at the distal end of the lower leg, sized and configured to engage the hooked end of the tab;
   b. distally extending walls disposed at the distal end of the lower leg, defining a passage configured to accommodate a portion of the tab;
   c. a first and a second apically extending serrated surface separated by a slot, the first and second serrated surface spanning a substantial portion of the lower leg, wherein the lower leg further defines an arcuate well disposed proximal to the first and second serrated surfaces of the lower leg, the arcuate well sized and configured to accommodate the basally extending arcuate guide rail.

5. The device of claim 4, wherein the elongated bar comprises: a first and a second beams extending proximally from a distally curved panel along a longitudinal axis, each of the first and second beams having:
   a. a distal end and a proximal end defining a T-shaped cross section;
   b. a proximal portion extending basally from a cross bar of the T-shaped cross section, forming a proximal rail having a protrusion at the proximal rails proximal end that is configured to enter and abut the proximal end of the closed proximal end of the apically open channel of the upper leg of each of the first and second clamps;
   c. a distal portion that is wider than the proximal rail, defining a ledge configured and sized to abut the distal end of the upper leg of each of the first and second clamps;
   d. a slot spanning the length of the proximal rail and distal portion configured to slidably couple to each of the first and second shelf centrally extending from the first and second side walls; and
   e. a resilient flat extension having an apically protruding lip extending from the proximal end of the beam's cross bar, the cross bar sized and configured to be accommodated in the first and second basally open channels of the clamps support.

6. A kit comprising:
   a. a first and a second identical clamps, each clamp comprising an upper leg and a lower leg hingedly coupled at a proximal end of the legs, being sized and configured to receive and clamp a portion of the umbilical cord transverse to the cord;
   b. a clamps' support having a distal end and a proximal end comprising a blade, the clamps' support sized and configured for supporting the clamps side by side with the blade between them and for guiding the clamps to advance the blade between the clamps to cut the umbilical cord, wherein the clamps' support comprises:
      a lower surface disposed basal and perpendicular to the central wall, and
      a basally curved wing hingedly coupled to the lower surface, wherein the basally curved wing is configured, when rotated to selectable cause the lower leg of each of the first and second clamps to be engaged by the upper leg of each of the first and second clamps; and
   c. an elongated bar, slidably coupled to the clamps' support, sized and configured for guiding the clamps in a sliding movement within the clamps' support to advance the blade between the clamps to cut the umbilical cord, wherein the clamps' support is configured for selectably clamping each of the pair of clamps onto the umbilical cord, wherein the first and the second identical clamps, the clamps' support and the elongated bar are capable of being assembled to form a device for clamping and cutting an umbilical cord by selectively moving between a first open position, an intermediate position and a cutting position.

7. The kit of claim 6, wherein the clamps' support further comprises:
   an apically curved wing extending apically from the upper surface;
   a first basally open channel defined between a first side wall, the upper surface and a central wall, sized and configured to slidably accommodate a portion of the first clamp's upper leg, the first basally open channel having a first shelf partially extending centrally from the first side wall spanning the length of the first basally open channel;
   a second basally open channel defined between a second side wall, the upper surface and the central wall, sized and configured to slidably accommodate a portion of the second clamp's upper leg, the second basally open channel having a second shelf partially extending centrally from the second side wall spanning the length of the second basally open channel;
   wherein the lower surface has a third apically open channel defined between a third side wall, the lower surface and the central wall, sized and configured to slidably accommodate a first portion of the first clamp's lower leg, and a fourth apically open channel defined between a fourth side wall, the lower surface and the central wall, sized and configured to slidably accommodate a first portion of the second clamp's lower leg; and a blade coupled to the central wall;

wherein the basally curved wing has an upper surface and a lower surface, the upper surface having a fifth apically open channel defined between a fifth side wall, the upper surface of the basally curved wing and a median sized and configured to slidably accommodate a second portion of the first clamp's lower leg, and a sixth apically open channel defined between a sixth side wall, the upper surface of the basally curved wing and a median sized and configured to slidably accommodate a second portion of the second clamp's lower leg.

8. The kit of claim 7, wherein the upper leg of each of the first and second clamps having a distal end and a proximal end, further comprising:
   a. an apically open channel having an open distal end and a closed proximal end configured to accommodate a portion of the elongated bar;
   b. a basally extending tab disposed at the distal end of the upper leg, the tab having a hooked end configured to engage an abutment disposed at a distal end of the lower leg;
   c. a first and a second basally extending serrated surface separated by a slot, the first and second serrated surface spanning a substantial portion of the upper leg; and
   d. a basally extending arcuate guide rail disposed proximal to the first and second serrated surfaces.

9. The kit of claim 8, wherein the lower leg of each of the first and second clamps having a distal end and a proximal end further comprising:
   a. the abutment disposed at the distal end of the lower leg, sized and configured to engage the hooked end of the tab;
   b. distally extending walls disposed at the distal end of the lower leg, defining a passage configured to accommodate a portion of the tab;
   c. a first and a second apically extending serrated surface separated by a slot, the first and second serrated surface spanning a substantial portion of the lower leg, wherein the lower leg further defines an arcuate well disposed proximal to the first and second serrated surfaces of the lower leg, the arcuate well sized and configured to accommodate the basally extending arcuate guide rail.

10. The kit of claim 9, wherein the elongated bar comprises: a first and a second beams extending proximally from a distally curved panel along a longitudinal axis, each of the first and second beams having:
   a. a distal end and a proximal end defining a T-shaped cross section;
   b. a proximal portion extending basally from a cross bar of the T-shaped cross section, forming a proximal rail having a protrusion at the proximal rails proximal end that is configured to enter and abut the proximal end of the closed proximal end of the apically open channel of the upper leg of each of the first and second clamps;
   c. a distal portion that is wider than the proximal rail, defining a ledge configured and sized to abut the distal end of the upper leg of each of the first and second clamps;
   d. a slot spanning the length of the proximal rail and distal portion configured to slidably couple to each of the first and second shelf centrally extending from the first and second side walls; and
   e. a resilient flat extension having an apically protruding lip extending from the proximal end of the beam's cross bar, the cross bar sized and configured to be accommodated in the first and second basally open channels of the clamps support.

* * * * *